United States Patent [19]
Larsson

[11] Patent Number: 4,929,229
[45] Date of Patent: May 29, 1990

[54] BREASTPUMP HAVING IMPROVED VALVE MECHANISM

[75] Inventor: Karl O. A. H. Larsson, Lindenweg, Switzerland

[73] Assignee: ISG/AG, Switzerland

[21] Appl. No.: 278,047

[22] Filed: Nov. 30, 1988

[51] Int. Cl.⁵ ............................................. A61M 1/00
[52] U.S. Cl. ..................................... 604/74; 604/320;
604/346; 119/14.25; 119/14.32; 137/511;
137/907
[58] Field of Search .................. 604/74, 319, 320, 346;
119/14.25, 14.26, 14.32, 14.33; 137/215, 384,
511, 533.17, 907

[56] References Cited

U.S. PATENT DOCUMENTS

| | | |
|---|---|---|
| 1,156,202 | 10/1915 | Barrett . |
| 1,184,293 | 5/1916 | Zeratsky . |
| 1,184,631 | 5/1916 | Leon . |
| 1,259,309 | 3/1918 | Somers . |
| 3,583,434 | 6/1971 | Muller . |
| 4,013,076 | 3/1977 | Puderbaugh et al. ............ 604/320 |
| 4,111,204 | 9/1978 | Hessel ................................ 604/320 |
| 4,311,141 | 1/1982 | Diamond . |
| 4,323,067 | 4/1982 | Adams . |
| 4,673,388 | 6/1987 | Schlensog et al. . |

FOREIGN PATENT DOCUMENTS

| | | |
|---|---|---|
| 108565 | 9/1939 | Australia . |
| 111477 | 9/1940 | Australia . |
| 121942 | 8/1946 | Australia . |
| 22323 | 7/1917 | Denmark . |
| 2658322 | 6/1978 | Fed. Rep. of Germany ........ 604/74 |
| 407293 | 9/1944 | Italy . |
| 1067982 | 10/1959 | Netherlands . |
| 158976 | 3/1957 | Sweden . |
| 762701 | 12/1956 | United Kingdom . |

Primary Examiner—Richard J. Apley
Assistant Examiner—Jennifer L. Doyle
Attorney, Agent, or Firm—Willian, Brinks, Olds, Hofer, Gilson & Lione

[57] ABSTRACT

An improved breastpump has a valve which closes off a path to a milk container in the presence of a negative pressure in the valve, and opens the path when the pressure is removed. The valve consists of a housing and a thin flexible membrane that is removably attached to the valve housing and covers a first opening in the housing through which milk can flow. The thin flexible membrane is preferably circular in shape with a knob formed in its center. The knob fits in a second opening in the housing in a snap-fit. This construction for the membrane assumes that it can never be mounted improperly. Raised bosses in the form of cone-shaped elevations are arranged around the perimeter of the flexible membrane. The cone-shaped bosses reinforce the membrane material and prevent the membrane from being drawn into the first opening.

6 Claims, 1 Drawing Sheet

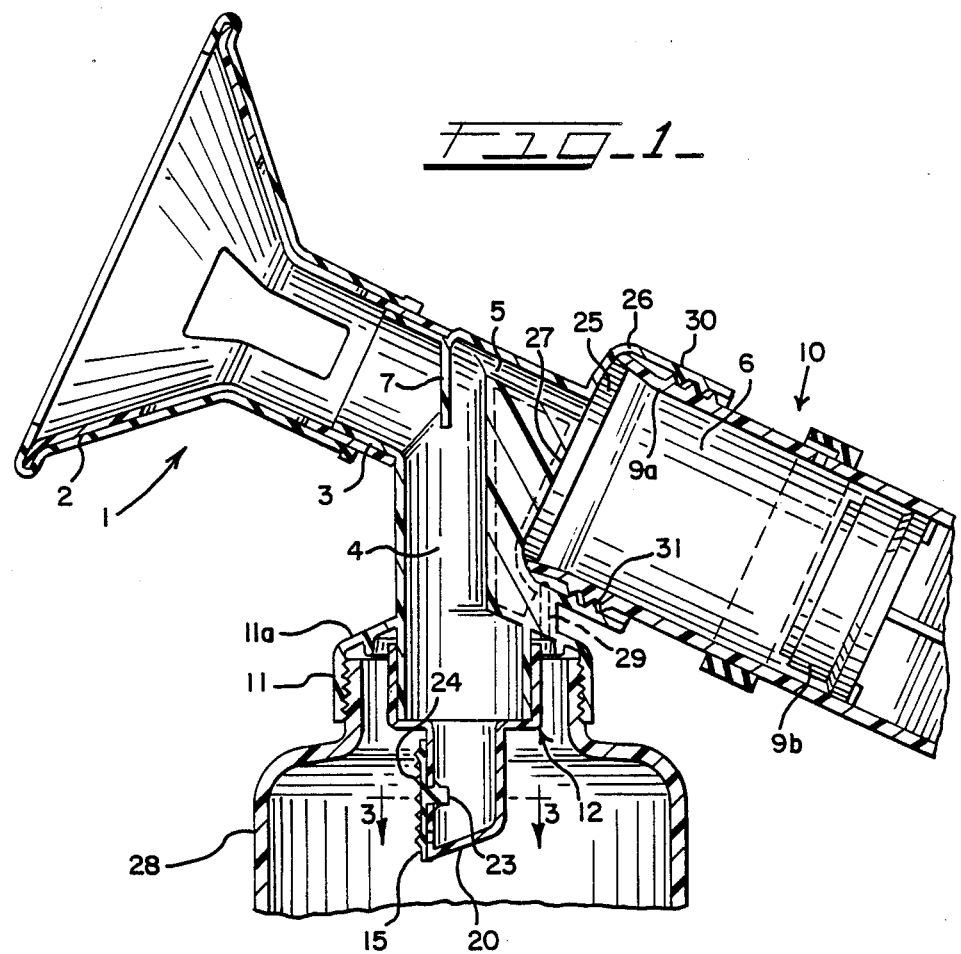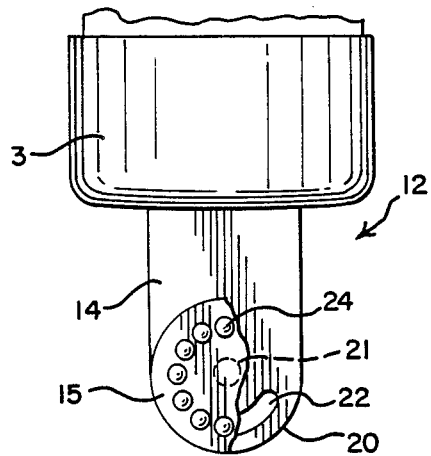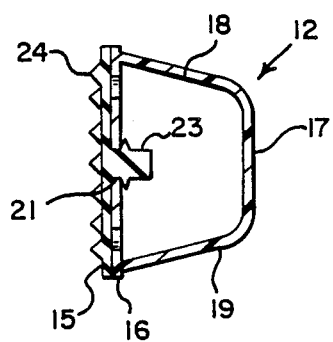

BREASTPUMP HAVING IMPROVED VALVE MECHANISM

FIELD OF THE INVENTION

The present invention generally relates to breastmilk pumps, and more particularly relates to a new and improved valving mechanism for a breastmilk pump.

BACKGROUND OF THE INVENTION

Breastmilk pumps are well known and are generally comprised of a hood that fits over the breast, a vacuum pump connected to the hood for generating an intermittent vacuum within the hood, and a receptacle for the expressed milk. Manually driven vacuum pumps as well as those that are driven by a motor are ordinarily used. The vacuum pumps of these devices, as a rule, intermittently generate a vacuum or negative pressure within the hood, with the hood encompassing the nipple and a substantial amount of the breast. The intermittent suction action of the pump serves to pull on the breast and thereby extract milk in an action reminiscent of suckling. The milk so extracted typically flows from the hood into a collection container, e.g., a bottle, for storage and later use. A breastpump of the foregoing type is shown in U.S. Ser. No. 07/053,055, filed May 22, 1987, now U.S. Pat. No. 4,857,051.

Apart from the purely hygienic requirements for such equipment, there are also certain technical problems to consider. One such significant problem is that varying degrees of vacuum can be generated as the milk receptacle fills, which must then be compensated for. A solution to this problem is to provide a valving mechanism which serves to regulate the negative pressure applied.

SUMMARY OF THE INVENTION

One of the principal objects of the present invention is to provide a breastpump that has a simple but effective valving mechanism which requires very little energy to operate the valve, and which is easily cleaned.

To these and other ends, the inventive breastpump comprises a hood to which a collecting or catch chamber is connected. At the outlet of the collecting chamber there is provided an improved valve which closes a passage leading from the collecting chamber to a receiving container. When a vacuum or negative pressure is applied to the hood from a suction device, which may be manually operated or motor driven, the valve closes the collecting chamber outlet to the receiving chamber. Upon release of the negative pressure, the valve opens the outlet. On the return cycle of the pump a positive pressure is applied to force the milk from the valve into the receiving container.

The valve used is extremely effective, simple in construction, and uses inexpensive, easily removable (disassembled) parts. In operation, the valve utilizes a minimum of mechanical movement from those parts. The preferred valve is constructed of two parts: a receptacle or housing member for briefly holding the expressed milk; and a thin flexible membrane that opens or closes an opening on the valve receptacle to control the flow of milk.

A circular design of the membrane, in its preferred form, prevents the membrane from being mounted on the receptacle in an incorrect manner. The membrane is formed in a single piece with an integral knob on its backside. The knob fits in an opening in the valve housing in a snap-like fit for ready removal for cleaning or replacement. Because of its circular shape with the knob in the center, the membrane cannot be improperly mounted.

Due to the provision of a collecting or catch chamber with a valve, milk can be pumped to a receiving container in the form of a plastic bag, since the negative pressure no longer affects the receiving container. Moreover, an overflow can be avoided, since the valve opens promptly and the expressed milk quickly flows into the receiving container.

A noteworthy advantage of the valving mechanism of the present invention is that, since the active element of the valve consists of a very thin and flexible rubber membrane, very little energy is required to open and close the valve. As noted, a relatively constant negative pressure or vacuum can be applied to the breastpump, since no variable volumes (i.e., in the receiving container), are present in this device. This also allows the employment of smaller pumps, since the volume under negative pressure can be reduced.

Another advantage of the valving mechanism of the present invention is in its overall construction. The valve utilizes inexpensive materials which are easily assembled and entail very little mechanical movement in its operation. This construction allows for inexpensive assembly, maintenance and repair and more reliable and durable operation (i.e. minimum of mechanical movement of parts).

The foregoing objects and advantages of the present invention will be further understood upon consideration of the following detailed description of the invention taken in conjunction with the accompanying drawings in which:

BRIEF DESCRIPTION OF THE DRAWINGS

FIG. 1 is a vertical sectional view of a breastpump and valve of the present invention;

FIG. 2 is an enlarged elevational view showing the valve of the present invention with a partial view of the flexible membrane; and FIG. 3 is an enlarged sectional view of the valve of FIG. 1 taken along line 3—3.

DETAILED DESCRIPTION OF THE INVENTION

The overall breastpump design used in conjunction with the present invention is generally shown in U.S. Pat. No. 4,857,051 for a breastpump, owned by the assignee of the present invention. The disclosure of that patent is incorporated herein by reference.

As seen in the accompanying FIG. 1, the breastpump comprises a hood body or hood member 1 having two ends. The first end 2 is funnel shaped and during operation is placed over the breast of the user. A second end 3 of the hood member is generally cylindrical in shape and communicates with a collecting or catch chamber 4, and with a vacuum line 6 via a short tubular extension 5. The vacuum line 6 leads to a pump 10, which can be manually or motor driven. A manual piston-type pump is shown, having a piston cylinder 9a and piston 9b.

Separating or baffle means in the form of a depending separation wall 7 forms a baffle between the end of the hood end 3 and the vacuum line. It will be noted that the bottom of the separation wall 7 is below the level of the bottom end of the tubular extension 5. Milk expressed into the hood member 1 is thus blocked by the separation wall 7 from thereby entering into the vacuum line 6. The breastpump is attached to a container 28 by a screw-on cap attachment via threaded collar 11.

At the lower portion of the collecting chamber 4 is the valve mechanism. The valve generally consists of a rigid plastic housing 12 and a thin flexible membrane 15 made of rubber or silicone rubber. The valve housing 12 has an upper section 13 and a lower section 14.

The upper section 13 is cylindrical in shape, and removably engages the outer portion of the outlet to the catch chamber 4 of the breastpump in a friction fit. The lower section 14 consists of four vertical walls and a bottom or floor portion. Walls 16 and 17 are opposite each other and parallel, and define the front and back of the valve, respectively. Wall 16 is longer and wider than wall 17. Walls 18 and 19 are sidewalls that are opposite each other. The intersection of the four walls 16, 17, 18 and 19 gives the impression of a trapezoid when viewed from the top, as shown in FIG. 3.

The bottom portion 20 of the lower section 14 is semicircular in shape, with a downward slope in the horizontal plane from wall 17 to wall 16, as best seen in FIG. 1.

Front wall 16 also defines two openings. An opening 21 is circular and is located at a point that is roughly at the center of a circle whose radius follows the intersection of front wall 16 and the bottom portion 20. A widened opening 22 is semicircular and formed through the front wall 16 along the bottom of the foregoing circle, adjacent the intersection of wall 16 and the bottom portion 20.

The thin flexible membrane 15 has a circular shape and is attached to the lower portion of the valve housing 12 by way of a knob 23 which is engaged in the opening 21 in a snap fit. The radius of the flexible membrane is large enough to completely cover the opening 22.

Raised bosses 24 in the form of cone-shaped elevations are arranged around the perimeter of the flexible membrane 15 and are located on the side of the membrane that is outboard to the wall 16. The cone-shaped bosses 24 reinforce the membrane material 15 and prevent the membrane 15 from being drawn into the opening 22. The bosses 24 are spaced inwardly from the edge of the membrane so as to overlie the opening 22 upon assembly.

The breastpump is operated by the manually driven piston pump 10. The forward end of the piston cylinder 9a abuts a shoulder 26 in an airtight fit. An annular collar 25 is formed around an endwall 27 to facilitate the airtight fit.

During the backstroke of the piston 9b, a negative pressure is created extending through the vacuum line 6 into the hood 2, collection chamber 4 and valve housing interior. The negative pressure pulls the flexible membrane 15 closed over the opening 22, thereby closing off the container 28, and trapping milk expressed from the user's breast in the valve housing 12. At the end of the backstroke of the piston 27 the negative pressure is released by a small hole in the sidewall of the cylinder 9a (not shown), thereby allowing a portion of any milk that has built up in the valve 12 to flow under gravity through the opening 22 into the container 28. The downward slope of the bottom portion of the valve facilitates the flow of milk through the second opening.

On the return stroke of the piston 27, air is forced through the vacuum line 6 into the collection chamber 4 and valve 11, thereby purging any excess milk that may remain in the bottom portion 20. The air is forced through the opening 22 into the container, and then through an internal channel 29, which extends between a canopy 11a of the screw-on collar 11 through to the interior of a connecting sleeve 30, to which the pump cylinder 9a is screwed. An airpath is provided from the sleeve interior by screw threads 31 on the sleeve 30 which are broken along their length to allow air to pass therethrough.

Thus, while the invention has been described with reference to a certain embodiment, those skilled in this art will recognize modifications of structure, arrangement, composition and the like that can be made to the present invention, yet will still fall within the scope of the invention as hereafter claimed.

I CLAIM:

1. In a breastpump comprising a hood body for placement over a breast, the hood body having a main funnel-shaped portion within which the breast is received and a tubular extension extending downstream from the main funnel portion, means for connecting the tubular extension of the hood body with a vacuum line to periodically withdraw air from the hood body in a manner that draws the breast into the main funnel portion and thereby expresses milk from the breast into the tubular extension, a baffle preventing milk from entering the vacuum line, a catch chamber for expressed milk connected with the tubular extension, the catch chamber being located downstream from the tubular extension and having an inlet and an outlet, the improvement comprising:

a valve mechanism having a housing including an upper portion removably attachable to said catch chamber outlet and a lower portion having a first widened opening defined in said lower portion through which milk can pass, and a thin flexible member sized to cover and close said first, widened opening when a negative pressure is applied within said housing and allow milk to pass through said first widened opening when said negative pressure is removed, said thin flexible member being removably mounted to said lower portion by a knob on said member which is inserted into a second opening defined in said lower portion.

2. The valve of claim 1 wherein said lower portion includes a vertical wall, said first being defined in said vertical wall widened opening adjacent a bottom to said lower portion, said second opening also being defined in said vertical wall.

3. The valve of claim 1 wherein said thin flexible member is circular in shape and has bosses located on a side of said member that is outboard to said lower portion, said bosses overlying said first widened opening, said bosses being of sufficient size to reinforce said thin flexible member to prevent said thin flexible member from being drawn into said first widened opening when said negative pressure is applied inside said housing.

4. In a breastpump comprising a hood body for placement over a breast, the hood body having a main funnel-shaped portion within which the breast is received and a tubular extension extending downstream from the main funnel portion, means for connecting the tubular extension of the hood body with a vacuum line to periodically withdraw air from the hood body in a manner that draws the breast into the main funnel portion and thereby expresses milk from the breast into the tubular extension, the vacuum line connecting means including a sleeve having interior threads to which a vacuum pump is threadably attached in an airtight engagement, said sleeve threads being broken in places, a catch chamber for expressed milk connected with the tubular extension, the catch chamber being located downstream from the tubular extension and having an inlet and an outlet which outlet communicates with a container to which the breastpump is attached in an airtight fit via a collared cap, the improvement comprising:

- a valve mechanism having a housing including an upper portion removably attachable to said catch chamber outlet and a lower portion having a first widened opening defined through said lower portion adjacent a bottom to said lower portion through which first widened opening milk can pass, and a thin flexible membrane sized to cover and close said first widened opening when a negative pressure is applied within said housing and allow milk to pass through said first widened opening when said negative pressure is removed, said thin flexible membrane being generally circular in shape and removably mounted to said lower portion by a knob formed integral with and at the center of said membrane, which knob is inserted into a second opening defined in said lower portion in a snap fit, said thin flexible membrane having bosses located on the side of the membrane that is outboard to said lower portion, said bosses overlying said first and widened opening and being of sufficient size to reinforce said thin flexible membrane to prevent said thin flexible membrane from being drawn into said first opening when said negative pressure is applied inside said housing member, and
- a closed airflow path provided in said breastpump for forcibly moving said thin flexible membrane away from said first opening and purging milk from said lower portion, said airpath extending from the vacuum line through the tubular extension and catch chamber into said valve mechanism, then through said first opening into the container, then through a passageway in the cap extending between the cap and the sleeve, and out from the sleeve through the broken threads.

5. The valve of claim 4 wherein said bottom to said lower portion has a downward slope in the direction of said first widened opening.

6. The value of claim 4 wherein said first widened opening is semi-circular and extends along a circumference of said bottom of said lower portion, and said bosses are arranged completely around and spaced inwardly from the perimeter of said thin flexible membrane.

* * * * *